United States Patent [19]

Tanno et al.

[11] Patent Number: 5,508,166

[45] Date of Patent: Apr. 16, 1996

[54] METHOD FOR THE MEASUREMENT OF REVERSE TRANSCRIPTASE USING IMMOBILIZED PRIMER

[75] Inventors: Masashi Tanno, Mishima; Junzo Mizoguchi, Tagata; Kouichi Sano, Takatsuki; Masuyo Nakai, Amagasaki, all of Japan

[73] Assignee: Asahi Kasei Kogyo Kabushiki Kaisha, Osaka, Japan

[21] Appl. No.: 207,255

[22] Filed: Mar. 8, 1994

Related U.S. Application Data

[63] Continuation of Ser. No. 773,277, Oct. 9, 1991, abandoned.

[30] Foreign Application Priority Data

Oct. 11, 1990 [JP] Japan .................................. 2-272749

[51] Int. Cl.$^6$ ...................................................... C12Q 1/68
[52] U.S. Cl. ........................................................... 435/6
[58] Field of Search ............................................. 435/5, 6

[56] References Cited

U.S. PATENT DOCUMENTS

| | | | |
|---|---|---|---|
| 3,755,086 | 8/1973 | Heimer | 195/103.5 R |
| 4,851,331 | 7/1989 | Vary et al. | 435/6 |
| 4,942,122 | 7/1990 | Imagawa et al. | |

FOREIGN PATENT DOCUMENTS

| | | |
|---|---|---|
| 0186526 | 7/1986 | European Pat. Off. |
| 0322922 | 7/1989 | European Pat. Off. |
| 0392459 | 10/1990 | European Pat. Off. |
| WO90/06373 | 6/1990 | WIPO |

OTHER PUBLICATIONS

Langer, P. R., et al., Enzymatic synthesis of biotih-labeled polynucleotides: Novel nucletic acid affinity probes. Proc. Natl. Acad. Sci. U.S.A. (Nov. 1981) 78:6633–6637.

Sano, K., et al., Antibody that inhibits human immunodeficiency virus reverse transcriptase and association . . . J. Cl. z. Microbiol. (Dec. 1987) 25:2415–2417.

Lund, V., et al., Assesment of methods for covalent binding of nucleic acids to magnetic beads, Dynabeads™, and the . . . Nucl. Acids. Res. (1988) 16:10861–10880.

Proc. Natl. Acad. Sci. vol. 78, No. 11, pp. 6633–6637, Nov. 1981 "Enzymatic synthesis of biotin-labeled . . . ".

Nature vol. 226 Jun. 27, 1970 pp. 1209–1211 "Viral RNA-dependent DNA Polymerase".

Nature vol. 226 Jun. 27, 1970 pp. 1211–1213.

Journal of Virological Methods, vol. 27, pp. 269–276, 1990, "A Solid Phase Reverse Transcriptase Micro-Assay For The Detection Of Human Immunodeficiency Virus And Other Retroviruses In Cell Culture Supernatants", P. A. Somogyi, et al.

*Primary Examiner*—George C. Elliott
*Attorney, Agent, or Firm*—Young & Thompson

[57] ABSTRACT

A method is provided for the determination of the presence of a reverse transcriptase in a sample liquid. In an aqueous medium, at least an adenine ribopolynucleotide RNA template (poly A), an immobilized oligodeoxythyminenucleotide and a biotinylated deoxyuridine triphosphate are reacted in the presence of the sample liquid. After separation of the reacted and the unreacted biotinylated deoxyuridine triphosphate from each other, the reacted or the unreacted biotinylated deoxyuridine triphosphate is detected. Also provided is a method for the determination of infection of a patient to a retrovirus. The reaction is conducted in the presence of a sample body fluid and the reverse transcriptase. After the detection of the reacted or the unreacted biotinylated deoxyuridine triphosphate, the reverse-transcriptase-neutralizing and/or inhibiting antibody titer in the sample body fluid is determined.

3 Claims, No Drawings

METHOD FOR THE MEASUREMENT OF REVERSE TRANSCRIPTASE USING IMMOBILIZED PRIMER

This is a continuation of application Ser. No. 07/773,277, filed Oct. 9, 1991, now abandoned.

BACKGROUND OF THE INVENTION

1) Field of the Invention

The present invention relates to a method for the determination of the presence of a reverse transcriptase in a sample liquid and also to a method for the determination of infection of a patient to a retrovirus on the basis of measurement of the reverse-transcriptase-neutralizing and/or inhibiting antibody titer in a sample body fluid.

2) Description of the Related Art

For the measurement of the activity of a reverse transcriptase, there has been reported a method in which a native RNA or adenine ribopolynucleotide (which may hereinafter be abbreviated as "poly A") and an oligodeoxythyminenucleotide (which may hereinafter be abbreviated as "oligo dT") and as a substrate, a tritium labeled deoxythymidine 5'-triphosphate (which may hereinafter be abbreviated as "[$^3$H]dTTP") are used, the oligo dT is allowed to elongate using the activity of the reverse transcriptase in a reaction mixture, the reaction mixture is filtered by a filter, and the residual radioactivity on the filter is then measured [David Baltimore, Nature, 226, 1209–1211 (1970); Howard M. Temin & Satoshi Mizutani, Nature, 226, 1211–1213 (1970)].

There has also been reported a method for the diagnosis of infection to an AIDS virus, a sort of retrovirus, by making use of the above-mentioned measurement method of the activity of a reverse transcriptase [Japanese Patent Application Laid-Open (Kokai) No. 252253/1988].

Many of the procedures which have heretofore been used commonly in biopharmaceutical research and recombinant DNA technology greatly rely upon the use of polynucleotides generally radiorabelled by isotopic hydrogen ($^3$H), phosphorus ($^{32}$P), carbon ($^{14}$C) or iodine ($^{126}$I). Such radioactive elements are employed as useful indicator probes because they can detect, monitor, localize or isolate nucleic acids or other scientifically or clinically interesting molecules even when such nucleic acids or molecules are present in a trace amount.

Stringent limitations are however imposed on the use of radioactive substances, resulting in serious drawbacks. As a first problem, for those handling a radioactive substance, there is a potential danger that they can be exposed to high-level radioactive rays. Careful and fail-free safety measures must be practiced during the production, use and post treatment of radioactive isotopes. A second problem resides in that a radioactive nucleotide is expensive and its use results in a higher cost in general applications. As a third problem, a radioactive substance of highly specific radioactivity must be used to obtain a necessary level of sensitivity. The radioactive substance of high specific radioactivity however has a short half-life correspondingly, so that its shelf life is limited. This imposes limitations on its use.

It has hence been studied to use a nonradioactive labeling substance in place of such a radioactive substance. It has however been reported, for example, that when a native mRNA as a template, oligo dT as a primer and a biotinylated deoxyuridine 5'-triphosphate (which may hereinafter be abbreviated as "biotin-dUTP") as a substrate were reacted using a reverse transcriptase derived from avian myeloblastosis virus, biotin-dUTP was not used at all as a substrate, no elongation of oligo dT was observed, and biotin-dUTP cannot therefore be used for the measurement of the activity of the reverse transcriptase [Pennina R. Langer, Alex A. Waldrop & David C. Ward, Proc. Natl. Acad. Sci. USA, 78, 6633–6637 (1981)]. Biotinylated nucleotides have therefore been considered to be unapplicable for the measurement of the activities of reverse transcriptases.

The present inventors previously conducted an extensive investigation with a view toward obtaining a measurement system for the activity of a reverse transcriptase without using any radioactive isotope. As a result, it was found that the use of a specific RNA template and a particular primer makes it possible to use biotin-dUTP as a substrate in the presence of a reverse transcriptase and the activity of the reverse transcriptase can thus be easily measured.

The above method, however, still involves some problems so that there has been a demand for their improvements. Described specifically, the above method is accompanied by the problems that it requires cumbersome procedures and some time is needed until measurement becomes feasible after initiation of the reaction. It has therefore been desired to develop a method which is simple in procedures and permits measurement in a short time.

SUMMARY OF THE INVENTION

With the foregoing problems in view, the present inventors have proceeded with a further investigation. As a result, it has been found that use of an immobilized primer can overcome the problems described above and can easily and quickly measure the activity of a reverse transcriptase, leading to the completion of the present invention.

In one aspect of the present invention, there is thus provided a method for the determination of the presence of a reverse transcriptase in a sample liquid, which comprises reacting, in an aqueous medium, at least an adenine ribopolynucleotide RNA template (poly A), an immobilized oligodeoxythyminenucleotide and a biotinylated deoxyuridine triphosphate in the presence of the sample liquid; and, after separation of the reacted and the unreacted biotinylated deoxyuridine triphosphate from each other, detecting the reacted or the unreacted biotinylated deoxyuridine triphosphate.

In another aspect of the present invention, there is also provided a method for the determination of infection of a patient to a retrovirus, which comprises reacting, in an aqueous medium, at least an adenine ribopolynucleotide RNA template (poly A), an immobilized oligodeoxythyminenucleotide and a biotinylated deoxyuridine triphosphate in the presence of a sample body fluid and the reverse transcriptase; and, after separation of the reacted and the unreacted biotinylated deoxyuridine triphosphate from each other, detecting the reacted or the unreacted biotinylated deoxyuridine triphosphate and determining the reverse-transcriptase-neutralizing and/or inhibiting antibody titer in the sample body fluid.

The method of the present invention has made it possible to detect the activity of a reverse transcriptase, for example, in a cultured media of lymphocytes from a HIV carrier without using any radioactive labeling substance. It has also become possible to detect the amount of the neutralizing and/or inhibiting antibody to the reverse transcriptase, said antibody being closely related to development of AIDS, without the need for any radioactive labeling substance. This has made it possible to easily monitor the danger of development of HIV symptoms by HIV virus carriers.

In particular, the method of the present invention uses the immobilized oligo dT so that the reaction time is short and the separation of the reacted and the unreacted reactants is extremely easy. The present invention has therefore made it possible to shorten the measurement time and further to process a number of samples. The method of the present invention is therefore convenient for automated practice.

Further, use of the poly A at a molar ratio of 0.3–1150 relative to the immobilized oligo dT leads to good sensitivity. More preferred measurement is feasible when the molar ratio of the poly A to the immobilized oligo dT is controlled at 7–70:1.

DETAILED DESCRIPTION OF THE INVENTION

In the present invention, poly A employed as a template can be artificially prepared, for example, by synthesizing the same using a gene manipulation technique or chemical synthesis technique. Poly A made of 100–500 bases can be mentioned as particularly preferred examples. Poly A of about 255 bases long on average can be mentioned as an example that can usually be employed advantageously.

The immobilized oligodeoxythyminenucleotide, which may hereinafter be abbreviated as an "immobilized oligo dT" acts as a primer A preferred example is an oligomer of deoxythymidine, said oligomer containing 11 or more bases. Although the longer are preferred, those usable advantageously in general are, for example, immobilized oligo dTs having an average strand length of from about 15 bases to about 21 bases.

The immobilized oligo dT is obtained by binding oligodeoxythyminenucleotide (oligo dT) on a solid carrier.

Although no particular limitation is imposed on the solid carrier, natural or synthetic, polymer carriers such as glass particles, cellulose or polystyrene can be used.

Of these, examples of synthetic polymer carriers include polystyrenes, i.e., homopolymers and copolymers of styrene and styrenes containing one or more sulfonyl, carboxyl and/or amino groups (hereinafter called "styrene derivative monomers"); copolymers between styrene or styrene derivative monomers and methylstyrene, ethylstyrene, chlorostyrene, ethylene, propylene, acrylic acid, methyl acrylate, ethyl acrylate, methacrylic acid, methyl methacrylate, ethyl methacrylate, acrylonitrile, acrylamide, maleic acid, fumaric acid, butadiene, chloroprene, isoprene, vinyl chloride, vinylidene chloride, vinyl acetate, vinyltoluene, divinylbenzene and the like; and copolymers with polyvinyltoluene, polyesters, polyacrylic acid, polymethacrylic acid, polyacrylonitrile, polyvinylpyrrolidone, poly vinyl acetate-acrylate, vinyl chlorideacrylate and the like. These synthetic polymer carriers may be surface-treated with a nonionic surfactant in advance.

Particularly preferred examples include homopolymers and copolymers of styrene, chlorostyrene, acrylic acid, vinyltoluene and methyl methacrylate.

To immobilize oligo dT on these solid carriers, either the adsorption technique or the chemical binding technique can be used. The chemical binding technique is preferred as it can provide higher sensitivity.

It is particularly preferred to chemically bind oligo dT to a solid carrier on the side of its 5'-terminal. For example, a phosphate group present at the 5'-terminal of oligo dT is activated in the presence of a condensing agent or the like and is then condensed with an amino group of a solid carrier having amino groups such as an amino-containing polystyrene or polypeptide or of a solid carrier with amino groups introduced therein. Described more specifically, the condensation can be conducted in the presence of a condensing agent such as 1-ethyl-3-(3-dimethylaminopropyl)carbodiimide hydrochloride, preferably by adding 1-methyl-imidazole.

As an alternative, an amino group is introduced beforehand to a phosphate group at the 5'-terminal of oligo dT in the presence of the above-described condensing agent. The amino group is then condensed, with dehydration, with a carboxyl group of a solid carrier having carboxyl groups such as a carboxyl-containing polystyrene or of a solid carrier with carboxyl groups introduced therein.

It is also possible to bind the oligo dT or the suitable functional groups modified oligo dT to a solid carrier which contains inherently or is introduced the functional groups such as sulfenyl, hydroxyl or dimethyl amino groups by using an appropriate spacer.

No particular limitation is imposed on the shape of the solid carrier oligo dT. Oligo dT can be coupled as a solid carrier on surfaces of balls, particles or fibers or on walls of a plate, cup or the like.

The amount of oligo dT coupled per unit surface area of the solid carrier generally gives maximum absorbance below the coupled amount of 5.0 pmol/cm$^2$. Measurement is still feasible at greater coupled amounts but unduly large coupled amounts are not preferred from the standpoints of sensitivity and economy. Preferably, the range of 0.15–5.0 pmol/cm$^2$ can be mentioned by way of example.

As the biotinylated deoxyuridine triphosphate (which may hereinafter be abbreviated as "biotin-dUTP" or a "labeling substrate") employed as a substrate, may be mentioned by way of example a compound in which a biotin group and an uracyldeoxynucleoside group are coupled together via a suitable spacer such as aminoaryl group. Exemplary specific compounds include compounds in which a biotinyl group is coupled with dUTP via a suitable spacer, such as 5-[N-(N-biotinyl-ε-aminocaproyl)- 3-aminoaryl]deoxyuridine triphosphates (biotin-11-dUTP) and 5-[N-[N-(biotinyl-ε-amino-caprolyl)-γ-aminobutyryl]-3-aminoaryl]-deoxyuridine triphosphates (biotin-16-dUTP). Biotin-11-dUTPs and biotin-16-dUTPs are compounds available on the market, and other compounds can also be easily prepared in accordance with the processes disclosed in known publications such as Japanese Patent Application Laid-Open (Kokai) No. 209297/1982.

As reagents useful for the detection of the amount of biotin and compositions thereof, it is possible to use those generally employed for the detection of the amount of biotin. Illustrative examples include fluorescein isothiocyanate (FITC) fluorescence detecting compositions, peroxidase detecting compositions, acidic phosphatase detecting compositions, alkaline phosphatase detecting compositions, and β-galactosidase detecting compositions.

Exemplary FITC fluorescence detecting compositions include compositions comprising rabbit biotin antibody IgG and FITC-conjugated goat anti-rabbit antibody IgG as well as FITC-conjugated avidin. Illustrative peroxidase detecting compositions include compositions comprising a streptavidin-biotinylated horseradish peroxidase complex, a suitable buffer such as phosphate buffer, o-phenylenediamine and hydrogen peroxide. Further, exemplary acidic phosphatase detecting compositions include compositions comprising a streptavidin-biotinylated acidic phosphatase complex, a suitable buffer such as phosphate buffer, and a chromogenic substance such as paranitrophenyl phosphate or a fluorescent substrate such as 4-methylumbelliferyl phosphate, while illustrative alkaline phosphatase detecting compositions include compositions comprising a streptavidin-biotinylated alkaline phosphatase complex, a suitable buffer such as tris-HCl buffer and a chromogenic substance such as paranitrophenyl phosphate or a fluorescent substance such as 4-methylumbelliferyl phosphate as well as compositions comprising an alkaline phosphatase labeled streptovidin, a suitable buffer such as tris-HCl, and a chromogenic substrate such as paranitrophenyl phosphate or a fluorescent substance such as 4-methylumbelliferyl phosphate. In addition, exemplary β-galactosidase detecting compositions include compositions comprising a streptavidin-β-galactosidase complex, a suitable buffer such as phosphate buffer and a chromogenic substrate such as 2-nitrophenyl-β-galactoside or a fluorescent material such as 4-methylumbelliferyl-β-galactoside.

As these compositions, it is possible to use those already available on the market or reagent compositions for the detection of biotin, said reagent compositions having been prepared in various ways with reference to known publications.

To practice the method of the present invention for the determination of the presence of a reverse transcriptase in a sample liquid, it is necessary firstly to react the poly A, the immobilized oligo dT and biotinylated dUTP in an arbitrary order and, subsequent to removal of unreacted biotinylated dUTP, to measure the amount of biotinylated dUTP.

Regarding the quantitative relation between the poly A (average strand length: 255 bases) and the immobilized oligo dT (average strand length: 21.5 bases), it is preferred to use the poly A and the immobilized oligo dT at a molar ratio of 1150:1 to 0.3:1. It is only necessary to use the poly A in an amount preferred in view of its amount to be coupled per unit area of the immobilized oligo dT.

The reaction can be conducted by incubating a sample liquid, the poly A, the immobilized oligo dT and biotinylated dUTP as a labeled substrate in a buffer, such as tris-HCl buffer or phosphate buffer adjusted to pH 6.5–8, around 37° C. for 0.5–24 hours so that the biotinylated dUTP is coupled to the primer portion of the poly A primered with immobilized dT under the action of the reverse transcriptase present in the system.

Any solution can be used as the sample liquid as long as it is intended to determine the presence or absence of a reverse transcriptase in the solution or to measure the enzymatic activity of the reverse transcriptase in the solution. Cultured media of retro-virus-infected cells can be mentioned by way of example.

Further, separation of the biotin-dUTP coupled to portion of immobilized oligo dT (which may hereinafter be referred to as the "reaction product") from the unreacted biotin-dUTP can be easily conducted by filtration, centrifugation, decantation or the like owing to the use of the immobilized oligo dT.

The amount of the biotinylated deoxyuridine employed as a substrate, namely, the amount of the reacted biotin-dUTP can be determined by detecting, the amount of biotin in the biotinylated deoxyuridine reacted to the portion of primer through the elongation step using a biotin-detecting reagent. When a composition comprising an alkaline phosphatase labeled streptabidin, tris-HCl buffer and paranitrophenyl phosphate is used as an exemplary reagent for the detection of the content of biotin, the detection of the amount of the biotin-dUTP can be practiced in the following manner.

An immobilized oligo dT reacted with the biotinylated dUTP is immersed for 10–60 minutes in a solution which has been obtained by adding an alkaline phosphatase conjugated streptavidin to a concentration of 0.05–10 μg/ml in tris-HCl buffer containing 0.15–0.5 M of NaCl and controlled at pH 7.5–9.5. The thus-immersed solid carrier is washed with a sufficient amount of the above buffer at least 3 times and is then immersed, for example, for 0.1–2 hours in a solution which has been obtained by dissolving 1 mg/ml of paranitrophenyl phosphate in a 50 mM diethanolamine-HCl buffer containing 1 mM of MgCl and controlled at pH 9.5–10, whereby the solid carrier is caused to develop a color. Quantitation of the intensity of the color so produced can be effected by measuring the absorbance at a wavelength of 405 nm.

Since the amount of the reacted biotin-dUTP thus measured reflects the amount of the reverse transcriptase in the system, namely, the amount of the reverse transcriptase in the sample liquid, the amount of the reverse transcriptase can be determined therefrom.

To increase the detection sensitivity, it is also possible to add deoxythymidine triphosphate (which may hereinafter be abbreviated "dTTP") as a substrate in addition to the labeling substrate. For this purpose, the dTTP can be used normally at a molar ratio of 2–20 times, preferably 3–4 times relative to the amount of the biotin-dUTP used as the labeling substrate.

The quantitative determination of the amount of the reverse transcriptase by the method of the present invention has good sensitivity so that the reverse transcriptase as little as 0.0001–1 unit or so can be usually quantitated.

Upon practice of the method of the present invention for determining infection of a patient to a retrovirus by detection of reverse transcriptase neutralizing and/or inhibiting antibody in a sample body fluid, it is necessary to use at least the biotin-dUTP as a substrate in the presence of a sample body fluid and a reverse transcriptase so that it is reacted with the poly A and immobilized oligo dT. This step can be carried out as will be described below next. A solution containing a reverse transcriptase whose enzymatic activity has been measured in advance is prepared usually in an amount of 0.001–1 unit/test, preferably in an amount of 0.001–0.01 unit/test. The reverse transcriptase-containing solution are mixed with sample body fluid, and then pre-incubated at about 4° C. usually for 0.1–2 hours, preferably for 10–60 minutes. The resulting solution is added to a buffer, such as Tris-HCl buffer having been adjusted to pH 6.5–8, which contains usually 0.5–100 μM, preferably 1–5 μM of biotin-dUTP as a substrate together with the poly A and immobilized oligo dT. The mixture so formed is then incubated at about 37° C. for 0.5–24 hours.

Exemplary usable reverse transcriptases include those obtained by subjecting viral particles of a retrovirus—such as human immunodeficiency virus type 1 (HIV-1), human immunodeficiency virus type 2 (HIV-2), simian immunodeficiency virus (SIV), mouse mammary tumor virus, human T-cell leukemia virus type I (HTLV-1), Rous avian sarcoma virus, Rous associated virus 2 (RAV-2) and hepatitis B virus (HBV) to solubilization with a non-ionic surfactant, for example, polyoxyethylene alkylphenyl ether (e.g., "Triton X-100", trade name; and "NP-40", trade name).

On the other hand, the sample body fluid may be any desired body fluid which is either contained or produced in the human body having an antibody against the reverse transcriptase. Serum is preferred.

The serum is normally employed in a form precipitated with a 30–50% saturated ammonium sulfate solution or in a form passed through a cation-exchange resin such as DEAE or QAE-Sephadex®.

The separation of the reacted and unreacted biotin-dUTP and the detection of their amounts can be conducted following the procedure of the above-described method for the determination of the presence of the reverse transcriptase.

The amount of the reacted or the unreacted biotin-dUTP in the measurement system can be determined as described above. It is to be noted that the reverse transcriptase in the system is deactivated by the antibody introduced from the sample body fluid and as a result, the amount of the reacted biotin-dUTP is decreased. Accordingly, the reverse transcriptase neutralizing and/or inhibiting antibody titer of the sample body fluid can be determined using as an index a positive control body fluid and a negative control body fluid. This antibody titer can be used as an index for the determination of infection or non-infection of the patient, to which the sample body fluid belongs, to the retrovirus.

In the invention, it is also preferred to control the quantitative relationship between the poly A (average strand length: 255 bases) and the immobilized oligo dT (average strand length: 21.5 bases) such that the molar ratio of the poly A to the immobilized oligo dT ranges from 1150:1 to 0.3:1. It is only necessary to use the poly A in an amount preferred in view of its amount to be coupled per unit area of the immobilized oligo dT.

To increase the detection sensitivity, it is also possible to add the dTTP as a substrate in addition to the labeling substrate. For this purpose, dTTP can be used normally at a molar ratio of 2–20 times, preferably 3–4 times relative to the amount of the biotin-dUTP used as the labeling substrate.

To advantageously practice the method of this invention, it is possible to use, for example, a kit for the detection of the amount of a reverse transcriptase, which comprises:

(i) a poly adenine RNA template;

(ii) an immobilized oligodeoxythyminenucleotide complementary to the RNA template;

(iii) a biotinylated deoxyuridine triphosphate; and (iv) a reagent for the detection of the amount of biotin.

In this kit, each reagent may be in the form of a solution. As an alternative, each reagent may be in a lyophilized form so that it can be dissolved with deionized water, physiological saline or one of various buffers upon use.

The present invention will hereinafter be described in further detail by the following examples. It should however be borne in mind that the present invention is not necessarily limited to or by the following examples.

EXAMPLE 1

Comparison in reaction velocity between a reverse transcriptase reaction using an immobilized primer and a liquid reverse transcriptase reaction system (1) Immobilization of oligo $dT_{12-18}$ to an Aminated Plate Oligo $dT_{12-18}$ (average strand length: 15 bases; average molecular weight: 4,950 dalton; product of Pharmacia AB) was dissolved to give 200 ng/50 µl in an aqueous solution containing 100 mM of 1-ethyl-3-(3-dimethylaminopropyl-)carbodiimide hydrochloride (hereinafter abbreviated as "CDI"; product of Peptide Institute, Inc.) and 100 mM of a 1-methylimidazole-HCl buffer adjusted to pH 7.0 (hereinafter abbreviated as "IMD"; product of Sigma Chemical Company). The resultant solution was poured in 50-µl portions in wells of an aminated plate (bottom area: 0.32 cm$^2$; product of Sumitomo Bakelite Co., Ltd.) and was reacted at room temperature for 24 hours. The surface area of each well, to which the reaction mixture was to be brought into contact, was 0.63 cm$^2$. After the reaction, the solution was discarded and each well was washed with 200 µl of 0.1M tris-HCl buffer which contained 0.15M of NaCl (pH: 7.5; hereinafter called "TBS"). The well was similarly washed twice with 200 µl of the buffer, whereby an immobilized primer (i.e., the plate with oligo $dT_{12-18}$ immobilized thereon) was obtained.

(2) Reverse Transcriptase Reaction using the Immobilized Prime

To conduct a DNA strand elongation reaction by the reverse transcriptase, 1 µg of poly A (average strand length: 255 bases; average molecular weight: 86,700 dalton; product of Pharmacia AB) and 0.4 nmol of biotin-11-dUTP (product of ENZO) were added to 50 µl of reaction buffer of twofold concentration [i.e., a buffer consisting of 100 mM tris-HCl buffer (pH 7.8), 24 mM dithiothreitol, 2.4 mM reduced glutathione, 20 mM $MgCl_2$, 320 mM KCl, 2 mM ethylene glycol tetraacetic acid, 0.4% "Triton X-100" (trade name) and 4% ethylene glycol]. The resultant solution was poured in the wells of the immobilized primer obtained as described above in Procedure (1). 50 µl portions of a reverse transcriptase [product of Takara Shuzo Co., Ltd.; derived from Rous associated virus 2(RAV-2)], which had been diluted to 15 mU/50 µl with a phosphate-buffered physiological saline (pH 7.4; hereinafter called "PBS"), were added to and mixed with the reaction solutions in the individual wells. The resultant mixtures were incubated at 37° C. for 1, 2, 3 and 24 hours, respectively.

(3) Detection of Enzyme Reaction Product (biotin-DNA)

To the individual reaction solutions obtained as described above in Procedure (2), 10 µl portions of 5M NaCl were added, respectively. After they were allowed to stand for 5 minutes, each well was washed with 200 µl of a 0.1M tris-HCl buffer which contained 0.5M of NaCl and 0.05M $MgCl_2$ (pH 9.5; hereinafter called the "washing solution"). Each well was similarly washed 2–4 times with 200 µl of the washing solution.

Next, 100 µl portions of a solution of 3% Bovine serum albumin (hereinafter called the "BSA") which dissolved in the washing solution were poured into the individual wells, followed by incubation at 37° C. for 1 hour. After the 3% BSA solution was discarded, each well was added with 50 µl of a 1000-fold dilution of alkaline phosphatase labeled streptavidin (final concentration: 0.088 µg/ml; product of BRL) in the washing solution, followed by incubation at room temperature for 1 hour.

Each well was similarly washed 3–5 times with 200 µl of the washing solution to eliminate any excess alkaline phosphatase labeled streptavidin. Residual enzymatic activity of alkaline phosphatase in the well was then measured to detect the amount of the biotin-DNA.

The measurement of the enzymatic activity of alkaline phosphatase was conducted by dissolving paranitrophenyl phosphate in a 50 mM diethanolamine-HCl buffer (pH 9.5), which contained 1 mM of $MgCl_2$, to give 1 mg/ml, adding 50 µl portions of the resulting solution to the individual wells, incubating the thus-formed mixtures at 37° C. for 30 minutes, adding 50 µl portions of 0.5 N NaOH to the individual wells to terminate the enzymatic reaction, and then measuring the absorbance of developed color of the individual wells based on the activity of alkaline phosphatase which is 405 nm of wavelength by means of a plate reader ("Model J-2000"; manufactured by InterMed Company).

The absorbances—which were obtained, respectively, when reacted for 1, 2, 3 and 24 hours by using 15 mU of the reverse transcriptase—are shown in Table 1.

TABLE 1

| Reaction time (hr) | Absorbance* |
|---|---|
| 1 | 0.639 |
| 2 | 1.521 |
| 3 | 1.867 |
| 24 | 2.773 |

$\lambda = 405$ nm

As is envisaged from the above results, the strand elongation reaction was found to have time dependency. Since it has been known in the above measurement method that reliable measurement data can be obtained at an absorbance of 0.1 or greater, it is understood that the method of the present invention permits detection as early as 1 hour after initiation of the reaction. Conversely, the comparative method (reaction in a liquid system) in Referential Example 1 to be given below finally permitted detection as late as 2 hours after the initiation of the reaction.

As has been demonstrated above, the method of the present invention, in which a reverse transcriptase reaction is conducted using an immobilized primer, can measure the activity of the reverse transcriptase in a shorter time than that required for the reaction in a liquid system and is therefore superior.

REFERENTIAL EXAMPLE 1

Time-Dependent Variations of a Reverse Transcriptase Reaction Product in a Liquid System To each 50 µl portion of the twofold-concentration reverse transcriptase reaction buffer described in Example 1(2), were added 1 µg of oligo $dT_{12-18}$, 0.1 µg of poly A and 0.4 nmol of biotin-11-dUTP. 15 mU of RAV-2 derived reverse transcriptase were added further to give a total volume of 100 µl. The resultant mixtures were incubated at 37° C. for 1, 2, 3 and 24 hours, respectively.

Each of the reaction mixtures was added with a tenfold amount of a solution which contained 1N hydrochloric acid and 0.1M of sodium pyrophosphate. The resultant mixture was stirred and then ice-cooled for 10 minutes. The solution thus obtained was subjected to suction filtration through a 100 $cm^2$ wide nylon membrane ("BIODYNE", trade mark; product of Nippon Pall Co., Ltd.) mounted on a 96-aperture filtration manifold (manufactured by BRL), whereby elongated biotinylated DNA strands were adsorbed on the nylon membrane.

Nylon membranes which were obtained above and carried biotinylated DNA strands adsorbed thereon were each added with 3% BSA dissolved in Buffer 1 [a buffer consisting of 0.1M tris-HCl buffer (pH 7.5) and 0.15M NaCl], followed by incubation at 65° C. for 1 hour. The nylon membrane with the biotinylated DNA strands adsorbed thereon was taken out from its BSA solution, and was then placed for 10 minutes in a 1000-fold dilution of alkaline phosphatase labeled streptavidin in Buffer 1. The dilution was employed in an amount of 7 ml per 100 $cm^2$ of the nylon membrane. The nylon membrane absorbing biotinylated DNA strands was thereafter exposed for 15 minutes to 100 ml of Buffer 1 to wash. Further, the nylon membrane was exposed twice in a similar manner.

The nylon membrane absorbing the biotinylated DNA strands was taken out and washed for 10 minutes with 100 ml of Buffer 2 [buffer consisting of 0.1M tris-HCl buffer (pH 9.5), 0.1M NaCl and 50 mM of $MgCl_2$].

The visualization of biotinylated DNA strand spot was conducted by placing the nylon membrane for 30 minutes in Buffer 2 which contained 0.33 mg/ml of nitroblue tetrazolium (NBT) and 0.17 mg/ml of 5-bromo-4-chloro-3-indolylphosphate (BCIP). The visualization solution was used in an amount of 7.5 ml per 100 $cm^2$ of the nylon membrane. Area intensities of color spots developed on the nylon membrane were measured at the wavelength of 550 nm by means of a densitometer ("CS-930", trade name; manufactured by Shimadzu Corporation).

Area intensities of the reaction products upon elapsed times of 1, 2, 3 and 24 hours, respectively, in the reverse transcriptase reaction by the liquid system are shown in Table 2.

TABLE 2

| Reaction time (hr) | Area intensity ($\times 10^3$) |
|---|---|
| 1 | 2.3 |
| 2 | 7.3 |
| 3 | 9.2 |
| 24 | 45 |

Under the above measurement conditions, reliable measurement is feasible at an area intensity of $7 \times 10^3$ or greater.

Accordingly, no detectable-significant area intensity was still available upon the elapsed time of 1 hour after the initiation of the reverse transcriptase reaction in the liquid system. Detectable-significant area intensities were obtained after 2 hours had passed since the initiation of the reaction.

EXAMPLE 2

Reverse transcriptase reaction when poly A and poly dA were both employed as templates To 50 µl portion of the reaction buffer of the twofold concentration described in Example 1(2), 0.24 nmol of biotin-11-dUTP, 0.96 nmol of dTTP (product of Boehringer Mannheim GmbH) and, as a template, 1 µg of poly A or poly dA were added. The resulting solution was poured into the individual wells of an immobilized plate of oligo $dT_{19-24}$ (average strand length: 21.5 bases; average molecular weight: 7,095 dalton; product of Pharmacia AB) which had been prepared following the procedure of Example 1(1). Next, 50 µl of a 1 mU/50 µl solution of a RAV-2 derived reverse transcriptase in PBS were added to the well. The resulting mixture was incubated at 37° C. for 18 hours so that the reverse transcriptase was allowed to act. Thereafter, amount of biotins incorporated to DNA strands so prolonged was measured by the method described in Example 1(3). Absorbances obtained when the reverse transcriptase was allowed to act while using poly A and poly dA as templates, respectively, are shown in Table 3.

TABLE 3

| Template | Absorbance* |
| --- | --- |
| Poly A | 1.256 |
| Poly dA | 0.004 |

$\lambda = 405$ nm

As is understood from the foregoing, reverse transcriptase did not act on poly dA. It was possible to specifically measure the reverse transcriptase by using the poly A, as template.

EXAMPLE 3

Study on the optimal amounts of oligo $dT_{19-24}$ and poly A on an aminated plate (1) Labeling of oligo $dT_{19-24}$:

To determine the most efficient primer/immobilized plate amount ratio for a reverse transcriptase reaction, the amount of oligo $dT_{19-24}$ actually conjugated to the wells of an aminated plate was investigated by a method to be described hereinafter. Firstly, 10 µg of oligo $dT_{19-24}$ were dissolved in 20 µl of water, followed by the addition of 2 µl of kination buffer of tenfold concentration [500 mM tris-HCl buffer (pH 7.6), 100 mM $MgCl_2$, 100 mM 2-mercaptoethanol], 1 µl of [$\gamma^{32}$P]ATP having 10 µCi/µl, and 1 µl of $T_4$ polynucleotide kinase of 20 units/µl.

By conducting incubation at 37° C. for 30 minutes, the 5'-terminal of oligo $dT_{19-24}$ was labeled with [$\gamma$-$^{32}$P]. Thirty minutes later, 2 ng of the reaction product were developed by paper chromatography (developer: 350 mM ammonium formate). The filter paper was dried and then divided into five equal sections. It was confirmed that radioactivity existed at the origin, in other words, oligo dT was labeled with [$\gamma$-$^{32}$P]. The filter paper which had been developed and divided into five equal sections was numbered as "1", "2", "3", "4" and "5" from the origin, and the radioactivity of each section was measured. The thus-measured radioactivity levels of the respective sections are shown in Table 4.

TABLE 4

| Developed fraction number | Radioactivity (cpm) |
| --- | --- |
| 1 (origin) | 4587 |
| 2 | 62 |
| 3 | 38 |
| 4 | 74 |
| 5 | 260 |

91% of the total radioactivity remained at the origin, namely, in the fraction where oligo $dT_{19-24}$ was localized, so that labeling of oligo $dT_{19-24}$ with [$\gamma$-$^{32}$P] was confirmed.

From Table 4, the following values were calculated:

Labeled percentage: 91%

Specific activity: $2.3 \times 10^6$ cpm/µg

The remaining reaction mixture was then added with 30 µl of water to give the total volume of 50 µl. An equivalent amount of phenol, which had in advance been saturated with 10 mM tris-HCl buffer (pH 7.5) containing 1 mM EDTA, was added. After the resultant mixture was stirred, the water layer was collected. The water layer was added with 5 µl of a 3M sodium acetate solution and 150 µl of chilled ethanol, and the mixture so formed was cooled at −80° C. for 15 minutes. After centrifugal separation, the supernatant was removed and the remaining pellet was washed twice with chilled 75% ethanol.

(2) Immobilization of oligo $dT_{19-24}$ on an aminated plate and quantitation of oligo $dT_{19-24}$ so conjugated:

The remaining pellet (labeled oligo dT) was dried in vacuo and then dissolved in water to give the concentration of 0.1 µg/µl. The solution was then diluted with the CDI- and IMD-containing aqueous solution described in Example 1(1) to give concentrations of 2,000 ng/50 µl, 200 ng/50 µl, 20 ng/50 µl, 2 ng/50 µl and 0.2 ng/50 µl. Their 50 µl portions were poured in individual wells of the aminated plate, followed by reaction at room temperature for 24 hours. After the reaction, the wells were washed as described in Example 1(1) and the levels of radioactivity still remaining in the respective wells were measured.

Table 5 shows the actual amounts of oligo $dT_{19-24}$ immobilized to the aminated plate—each of said amounts having been calculated from the radioactivity remaining in a well of the aminated plate based on the specific activity ($2.3 \times 10^6$ cpm/µg) and average molecular weight (7.095 dalton) of the radio-labeled oligo dT. It also shows the molar numbers of oligo $dT_{19-24}$ per $cm^2$ unit surface area calculated from the actual amounts of immobilized oligo $dT_{19-24}$ and the surface areas (0.63 $cm^2$) of the wells, with which surface areas the oligo dT reaction solutions were brought into contact.

TABLE 5

| Amount of oligo dT used (ng) | Radioactivity on well (cpm) | Amount of oligo dT conjugated (ng) | Amount of oligo dT conjugated per unit surface area (pmol/cm2) |
| --- | --- | --- | --- |
| 0.2 | 278 | 0.12 | 0.027 |
| 2 | 1,647 | 0.71 | 0.159 |
| 20 | 13,003 | 5.67 | 1.269 |
| 200 | 26,555 | 11.58 | 2.592 |
| 2,000 | 47,798 | 20.8 | 4.655 |

From the above results, it is envisaged that the amount of oligo $dT_{19-24}$ immobilized to each well of the aminated plate increases in proportion to the amount of oligo $dT_{19-24}$ added. When oligo $dT_{19-24}$ was added in the amount of 2,000 ng, 20 ng of oligo $dT_{19-24}$ was immobilized per well.

Each well of the aminated plate was in the form of a cylinder having a bottom area of 0.32 $cm^2$. Since the total amount of the liquid in the binding reaction of oligo $dT_{19-24}$ was 50 µl, the surface area in each well to which surface area oligo $dT_{19-24}$ can bind was 0.63 $cm^2$. The average molecular weight of oligo $dT_{19-24}$ (average strand length: 21.5 bases) is 7,095 dalton. The amount of oligo $dT_{19-24}$ immobilized per unit surface area of well was up to about 4.655 pmol/$cm^2$.

(3) Study on the optimal amounts of a template and a immobilized primer in a DNA strand elongation reaction by a reverse transcriptase:

To each of 50 µl portions of the reaction buffer of the twofold concentration described in Example 1(2), were added 0.24 nmol of biotin-11-dUTP and 0.96 nmol of dTTP. The resulting mixtures were further added with 10 µg, 1 µg, 100 ng, 10 ng and 1 ng of poly A (average strand length: 255 bases; average molecular weight: 86,700 dalton), respectively. Each of the mixtures so formed was poured into the individual wells of a immobilized plate, to which wells oligo $dT_{19-24}$ had been bound in the respective amounts determined in Example 3 (2). Next, 50 µl of an RAV-2 derived reverse transcriptase which had been adjusted with PBS to 0.1 mU/50 µl were added to each well. After mixing, the mixture was incubated at 37° C. for 18 hours so that the reverse transcriptase was allowed to act. Thereafter, the elongated biotin-DNA was measured by the method described in Example 1(3).

Table 6 shows absorbances obtained when 0.1 mU of the RAV-2 derived reverse transcriptase was allowed to act at 37° C. for 18 hours on the combinations of the various amounts of poly A and the various amounts of immobilized oligo $dT_{19-24}$.

TABLE 6

| oligo dT (ng) | dT (pmol) | Poly A | A (pmol) | Absor-bance* | A:dT(1) molar ratio |
|---|---|---|---|---|---|
| 0.12 ng | 0.01692 | 1 | 0.0115 | 0.006 | 0.680 |
| (0.027 pmol/ | | 10 | 0.115 | 0.008 | 6.797 |
| cm2) | | 100 | 1.15 | 0.013 | 67.967 |
| | | 1,000 | 11.5 | 0.016 | 679.669 |
| | | 10,000 | 115 | 0.014 | 6,796.690 |
| 0.71 ng | 0.10011 | 1 | | 0.010 | 0.115 |
| (0.159 pmol/ | | 10 | | 0.014 | 1.149 |
| cm2) | | 100 | | 0.025 | 11.487 |
| | | 1,000 | | 0.068 | 114.874 |
| | | 10,000 | | 0.091 | 1,148.736 |
| 5.67 ng | 0.79947 | 1 | | 0.016 | 0.014 |
| (1.269 pmol/ | | 10 | | 0.030 | 0.144 |
| cm2) | | 100 | | 0.056 | 1.438 |
| | | 1,000 | | 0.081 | 14.385 |
| | | 10,000 | | 0.098 | 143.845 |
| 11.58 ng | 1.63278 | 1 | | 0.030 | 0.007 |
| (2.592 pmol/ | | 10 | | 0.052 | 0.070 |
| cm2) | | 100 | | 0.088 | 0.704 |
| | | 1,000 | | 0.120 | 7.043 |
| | | 10,000 | | 0.123 | 70.432 |
| 20.8 ng | 2.93280 | 1 | | 0.023 | 0.004 |
| (4.655 pmol/ | | 10 | | 0.068 | 0.039 |
| cm2) | | 100 | | 0.085 | 0.392 |
| | | 1000 | | 0.111 | 3.921 |
| | | 10,000 | | 0.114 | 39.212 |

*= 405 nm

From the above results, it has been found that the amount of oligo $dT_{19-24}$ (average strand length: 21.5 bases; average molecular weight: 7,095 dalton) bound to an aminated plate, said amount being required to obtain a reliable minimum absorbance (about 0.1 or so), is at least 0.7 ng (i.e., 0.15 pmol/cm$^2$) or so, preferably about 10 ng (i.e., 2.6 pmol/cm2). No substantial difference was observed in absorbance even when the oligo dT was immobilized in amounts greater than the above-mentioned level.

It has also been found that the amount of poly A (average strand length: 255 base; average molecular weight: 86,700 dalton), said amount being required to obtain an absorbance of about 0.1 at an immobilized oligo $dT_{19-24}$ amount in the above range, is at least 100 ng (i.e., 1.83 pmol/cm$^2$), preferably from 1 µg (i.e., 18.3 pmol/cm$^2$) to 10 µg (i.e., 183 pmol/cm$^2$). From the foregoing, it has been found most preferable to use the poly A and immobilized oligo $dT_{19-24}$ in combination at a molar ratio of 1150:1 to 0.3:1, more preferably 70:1 to 7:1 for the reverse transcriptase.

EXAMPLE 4

At the combination of 10 ng of immobilized oligo $dT_{19-24}$ and 1 µg of poly A, said combination being one of suitable conditions determined from the results of the above examples, a reverse transcriptase reaction was conducted at 37° C. for 18 hours in accordance with the procedures of Example 2.

The reaction was conducted by changing the amount of the RAV-2 derived reverse transcriptase to 0, 0.01, 0.1, 1 and 10 mU (the solution amount will hereinafter be 50 µl). The absorbance was measured in accordance with the procedures of Example 1(3), whereby the absorbances shown in Table 7 were obtained. As is apparent from the table, the absorbance has been found to depend on the amount of the enzyme.

TABLE 7

| Reverse transcriptase (mU) | Absorbance* |
|---|---|
| 0 | 0 |
| 0.01 | 0.017 |
| 0.1 | 0.138 |
| 1 | 1.175 |
| 10 | 2.724 |

$\lambda = 405$ nm

EXAMPLE 5

Detection of an antibody against the activity of a reverse transcriptase:

Molt-4 cells (purchased from Dainippon Pharmaceutical Co., Ltd.) were infected with human immunodeficiency virus (HIV). These cells were cultured in RMPI-1640 medium (product of Gibco) supplemented with 10% fetal calf serum under the 5% of carbon dioxide gas concentration at 37° C. for about 2 weeks. The cultured medium was centrifuged at 30,000 rpm for 1 hour, whereby a pellet of viral particles ($10^6$ particles) was obtained. The pellet was suspended in a buffer which consisted of 0 5% of "Triton X-100", 0.8M of NaCl, 0.5 mM of phenylmethylsulfonyl fluoride, 20% of glycerin and 50 mM tris-HCl buffer (pH 7.8), so that an enzyme solution was prepared.

On the other hand, serum collected from an HIV infected patient was diluted twentyfold with 50 mM ethylenediamine-acetic acid buffer (pH 7.0). 1 ml of the diluted solution was caused to pass through a "QAE-Sephadex A-50" column (gel bed: 1 ml). Its throughpass fraction (4 ml) was used as a partially-purified antibody to the reverse transcriptase.

First, 25 µl portions of the above-described enzyme solution were mixed with 25 µl of the antibody stock, 25 µl of a 1/10 dilution of the antibody stock, 25 µl of a 1/100 dilution of the antibody stock and PBS, respectively, followed by incubation at 4° C. for 30 minutes. The residual activities of the reverse transcriptase in the mixtures were separately measured by the measurement method described in Example 2. As a result, absorbances as shown in Table 8 were obtained. The reverse transcriptase neutralizing and/or inhibiting antibody contained in the serum was therefore detected.

TABLE 8

| Dilution of antibody (times) | Absorbance* |
|---|---|
| × 1 | 0.028 |
| × 10 | 0.251 |
| × 100 | 0.631 |
| (No antibody) | 0.744 |

$\lambda = 405$ nm

EXAMPLE 6

Reverse transcriptase reactions at different oligo dT strand lengths

By the method described in Example 1(1), 200 ng portions of oligo dT samples (all, products of Pharmacia AB) whose strand lengths were 8, 10, 12, 15, 12–18, 19–24, 25–30 and 272 bases, respectively, were immobilized on an aminated plate. Under the conditions of Example 2, 0.1 mU of the reverse transcriptase was caused to act while using 1 µg of poly A. Elongated biotin-DNAs were then measured following the method described in Example 1(3).

The relationship of the length of oligo dT and the degree of absorbance is depicted in Table 9. The absorbance increased with the strand length of oligo dT. No preferable results were brought about at a strand length of 10 bases or shorter, while good results were brought about at a strand length of 12 or longer. It has therefore been confirmed that the usable strand length is usually 11 bases or longer.

TABLE 9

| Strand length of oligo dT (bases) | Absorbance* |
|---|---|
| 8 | 0.008 |
| 10 | 0.049 |
| 12 | 0.092 |
| 15 | 0.107 |
| 12–18 | 0.114 |
| 19–24 | 0.208 |
| 25–30 | 0.481 |
| 272 | 0.687 |

$\lambda = 405$ nm

EXAMPLE 7

Variations of detection sensitivity for biotin-DNA at different amounts of dTTP added Forty five µl portions of the reaction buffer of the twofold concentration described in Example 1(2) were taken on a plate with oligo $dT_{19-24}$ fixed thereon in accordance with the method described in Example 1(1), followed by the addition of 1 µl of 1 µg/µl of poly A. On the other hand, biotin-11-dUTP and dTTP were mixed at the following mixing molar ratios: 1:0, 1:3, 1:4, 1:5.7, 1:9, 1:12.3, 1:19, 1:24, 1:29, 1:39, 1:49 and 1:99. Those mixed solutions were prepared such that the final concentration of the sum of biotin-11-dUTP and dTTP became 0.3 mM. 4 µl (1.2 nmol) portions of those 0.3 mM mixtures of biotin-11-dUTP and dTTP were added to the above-mentioned plate with the oligo $dT_{19-24}$ immobilized thereon, and were mixed with a solution composed of the reaction buffer and 1 µg of poly A. Each well was also added with 50 µl of a RAV-2 derived reverse transcriptase adjusted with PBS to 1 mU/50µl. After mixing, they were incubated at 37° C. for 18 hours. The resulting biotin-DNAs were detected in accordance with the procedure described in Example 1(3). The absorbances at different mixing molar ratios of biotin-11-dUTP and dTTP are shown in Table 10.

TABLE 10

| Mixing molar ratio (biotin-dUTP:dTTP) | Absorbance* |
|---|---|
| 1:0 | 1.575 |
| 1:3 | 1.859 |
| 1:4 | 1.910 |
| 1:5.7 | 1.780 |
| 1:9 | 1.649 |
| 1:12.3 | 1.520 |
| 1:19 | 1.351 |
| 1:24 | 1.124 |
| 1:29 | 1.052 |
| 1.39 | 0.895 |
| 1:49 | 0.752 |
| 1:99 | 0.442 |

$\lambda = 405$ nm

As is apparent from the above results, the best sensitivity was obtained when the mixing molar ratio of biotin-11-dUTP to dTTP was 1:4.

EXAMPLE 8

Reverse transcriptase reaction on a carboxylated plate with oligo dT primer immobilized thereon 200 ng of oligo $dT_{20}$ which had been modified an amino group to the phosphoric group at the 5'-terminal and synthesized by a DNA synthesizer ("CYCLON"; manufactured by Biosearch Company) were dissolved in 25 µl of water. The resultant solution was placed in a well of a "CARBOPLATE" (manufactured by Sumitomo Bakelite Co., Ltd.). Then, 25 µl of a 200 mM IMD solution containing 200 mM of CDI were poured into the well. The solutions were mixed and then incubated at room temperature for 24 hours. After the reaction, the mixture was discarded, and the well was washed three times with 200 µl of TBS to provide an immobilized primer.

Separately using 0.1 mU, 0.5 mU, 1 mU and 10 mU of the RAV-2 derived reverse transcriptase, measurement was conducted in accordance with the method described in Example 2. The absorbances obtained when the strand elongation reaction was conducted at the reverse transcriptase amounts of 0.1 mU, 0.5 mU, 1 mU and 10 mU are shown in Table 11. It was permitted to measure those amount of the reverse transcriptase.

TABLE 11

| Reverse transcriptase (mU) | Absorbance* |
|---|---|
| 0.1 | 0.104 |
| 0.5 | 0.486 |
| 1 | 0.758 |
| 10 | 2.53 |

$\lambda = 405$ nm

EXAMPLE 9

Reverse transcriptase reaction on a microplate covered with oligo $dT_{19-24}$ by exposure to ultraviolet rays Oligo $dT_{19-24}$ (200 ng) was dissolved in 50 µl of PBS which contained 0.1M of $MgCl_2$. The resultant solution was taken on a microtiter plate (manufactured by Sumitomo Bakelite Co., Ltd.) and was left over at room temperature for 24 hours. After discarding the solution, the microfilter plate was exposed to ultraviolet rays having a wavelength of 254 nm for 3 minutes so that oligo $dT_{19-24}$ was immobilized on the plate. The well was washed three times with 200 µl of TBS. Using the well, a reverse transcriptase reaction was conducted under the same conditions as in Example 8. The absorbances obtained when the strand elongation reaction was conducted at the reverse transcriptase amounts of 0.1 mU, 0.5 mU, 1 mU and 10 mU are shown in Table 12.

TABLE 12

| Reverse transcriptase (mU) | Absorbance* |
|---|---|
| 0.1 | 0.018 |
| 0.5 | 0.091 |
| 1 | 0.141 |
| 10 | 1.239 |

$\lambda = 405$ nm

What is claimed is:

1. A method for measuring activity of a reverse transcriptase in a sample liquid, wherein said reverse transcriptase is that produced by human immunodeficiency virus type 1 (HIV-1), human immunodeficiency virus type 2 (HIV-2), simian immunodeficiency virus (SIV), mouse mammary tumor virus, human T-cell leukemia virus type 1 (HTLV-1), Rous avian sarcoma virus, Rouse associated virus 2 (RAV-2) or hepatitis B virus (HBV), said method comprising reacting, in an aqueous medium, at least an adenine ribonucleotide RNA template (poly A), an immobilized oligodeoxythymidine nucleotide, a biotinylated deoxyuridine triphosphate and deoxythymidine triphosphate in the presence of the sample liquid, and, after separation of the reacted and the unreacted biotinylated deoxyuridine triphosphate from each other, detecting the reacted or unreacted biotinylated deoxyuridine triphosphate by absorptiometry, wherein said deoxythymidine triphosphate is present in a molar ratio of 3–9 relative to said biotinylated deoxyuridine triphosphate.

2. The method of claim 1, wherein the immobilized oligodeoxythymine nucleotide is an oligodeoxythymine nucleotide in which the oligodeoxythymine nucleotide and a solid carrier are chemically bonded together.

3. The method of claim 1, wherein said deoxythymidine triphosphate is present in a molar ratio of 3–4 relative to said biotinylated deoxyuridine triphosphate.

* * * * *